United States Patent [19]

Kukes

[11] Patent Number: 4,948,768
[45] Date of Patent: Aug. 14, 1990

[54] CATALYST COMPOSITION FOR OLIGOMERIZATION OF OLEFINS

[75] Inventor: Simon G. Kukes, Naperville, Ill.; Jesse R. Harris; Robert L. Banks, both of Bartlesville, Okla.

[73] Assignee: Phillips Petroleum Company, Bartlesville, Okla.

[21] Appl. No.: 383,108

[22] Filed: Jul. 20, 1989

Related U.S. Application Data

[62] Division of Ser. No. 198,947, May 26, 1988, Pat. No. 4,879,425.

[51] Int. Cl.$^5$ ............................ B01J 29/02; B01J 21/16
[52] U.S. Cl. ................................................ 502/63; 502/84
[58] Field of Search .................................. 502/63, 84

[56] References Cited

U.S. PATENT DOCUMENTS

| | | | |
|---|---|---|---|
| 2,824,089 | 2/1958 | Peters et al. | 585/523 X |
| 3,271,475 | 9/1966 | Weesner | 585/510 |
| 3,431,316 | 3/1969 | Banks | 260/683 |
| 3,639,268 | 2/1972 | Jaffe et al. | 502/63 |
| 3,664,971 | 5/1972 | Jaffe | 502/84 |
| 3,691,144 | 9/1972 | Zuech | 585/520 X |
| 3,728,415 | 4/1973 | Arganbright | 585/510 |
| 3,764,636 | 10/1973 | Echigoya et al. | 585/510 |
| 3,766,292 | 10/1973 | Wall et al. | 260/670 R |
| 3,791,963 | 2/1974 | Jaffe | 502/84 |
| 3,795,606 | 5/1974 | Jaffe | 502/84 |
| 3,804,917 | 4/1974 | Shepard et al. | 585/533 |
| 3,862,257 | 1/1975 | Buben et al. | 585/523 |
| 4,415,473 | 11/1983 | Hinnenkamp | 252/373 |
| 4,442,223 | 4/1984 | Chester et al. | 502/64 |
| 4,446,244 | 5/1984 | Van Nordstrand | 502/84 |
| 4,465,892 | 8/1984 | Jacobs et al. | 585/666 |
| 4,507,400 | 5/1985 | Miller et al. | 502/84 |
| 4,531,014 | 7/1985 | Gregory et al. | 502/84 |
| 4,595,667 | 6/1986 | Takase et al. | 502/63 |
| 4,613,719 | 9/1986 | Kukes et al. | 585/528 |
| 4,637,991 | 1/1987 | Battiste et al. | 502/84 |
| 4,659,688 | 4/1987 | Kukes et al. | 502/208 |
| 4,719,191 | 1/1988 | Battiste et al. | 502/84 |
| 4,742,033 | 5/1988 | Harris et al. | 502/68 |
| 4,766,099 | 8/1988 | Dufresne et al. | 502/84 |

Primary Examiner—Patrick P. Garvin
Assistant Examiner—George R. Fourson
Attorney, Agent, or Firm—K. K. Brandes

[57] ABSTRACT

A composition comprises a physical mixture of (i) an oxide of molybdenum and/or tungsten supported by a silica-containing material and (ii) a pillared interlayered clay. This composition is used as catalyst in the conversion of $C_2$–$C_4$ monolefins to $C_5$–$C_{12}$ hydrocarbons.

18 Claims, No Drawings

CATALYST COMPOSITION FOR OLIGOMERIZATION OF OLEFINS

This is a division of copending application Ser. No. 198,947, filed May 26, 1988, now U.S. Pat. No. 4,879,425.

BACKGROUND OF THE INVENTION

This invention relates to a process for converting lower monoolefins to higher hydrocarbons which are useful as liquid fuels.

The oligomerization of gaseous monoolefins so as to form gasoline-type hydrocarbons is known and has been disclosed in the patent literature, such as in U.S. Pat. No. 4,613,719. However, there is an ever present need to develop new oligomerization processes employing more effective and/or less expensive catalyst compositions.

SUMMARY

It is an object of this invention to provide a novel composition of matter. It is another object of this invention to convert lower monoolefins having 2 to 4 carbon atoms per molecule to higher hydrocarbons having 5 to 12 carbon atoms per molecule. It is a further object to convert propylene to hydrocarbons containing at least 5 carbon atoms per molecule.

In accordance with this invention, a process for oligomerizing monoolefins comprises contacting
 (a) a feed which comprises at least one monoolefin containing 2 to 4 carbon atoms per molecule with
 (b) a catalyst composition comprising a physical mixture of
  (i) a metal oxide selected from the group consisting of tungsten oxide, molybdenum oxide and mixtures theroef, said metal oxide being supported by a solid silica-containing material, and
  (ii) a pillared interlayered clay; under such contacting conditions as to obtain a product comprising at least one hydrocarbon which contains 5 to 12 carbon atoms per molecule.

In a preferred embodiment, said monoolefin is propylene. In another preferred embodiment, formed hydrocarbons containing from 5 to 12 carbon atoms per molecule are separated from said product and recovered.

Also in accordance with this invention, a composition of matter comprising a physical mixture of (i) and (ii), as defined above, is provided.

DETAILED DESCRIPTION OF THE INVENTION

Any feed which contains at least one monoolefin having 2-4 carbon atoms per molecule can be employed. Examples of suitable feed olefins are ethylene, propylene, 1-butene, 2-butene and 2-methyl-propylene. Presently preferred is propylene. The monoolefin feed stream can contain inert gases such as nitrogen and helium or gaseous paraffins such as methane and ethane.

The composition of matter of this invention, which is employed as catalyst in the process of this invention, is a mixture (physical blend) of two components. Component (i) is molybdenum oxide and/or tungsten oxide (preferably tungsten oxide) supported by a silica-containing material (preferably consisting essentially of silica). Compound (ii) is a pillared interlayered clay. Any suitable weight ratio of (i) to (ii) can be employed. Generally, the weight ratio of component (i) to component (ii) in the catalyst composition is in the range of from about 1:10 to about 5:1, preferably from about 1:4 to about 1:1. Components (i) and (ii) can be mixed by any suitable mixing method, preferably dry-blending. Components (i) and (ii) can be present in any suitable shape, e.g., as powders, pellets, granules, agglomerates, extrudes, and the like.

Component (i) can be prepared by any suitable means, such as those disclosed in U.S. Pat. No. 3,431,316, the disclosure of which is herein incorporated by reference. Preferably, silica is impregnated with a dissolved compound of tungsten (such as an ammonium tungstate), followed by drying and calcining (preferably in a free oxygen containing atmosphere, at a temperature high enough to obtain tungsten oxide). The weight percentage of the metal oxide (i.e., Mo oxide or W oxide or a mixture of both, preferably $WO_3$) in compound (i) generally is in the range of from about 1 to about 20 weight-%, preferably about 2-8 weight-%. The weight percentage of the silica in component (i) generally is in the range of from about 80 to about 99 weight-%, preferably about 92-98 weight-% $SiO_2$.

Component (ii), i.e., the interlayered pillard clay material, can be prepared by any of the well known methods of reacting a clay, preferably a smectite clay (more preferably bentonite), with an aqueous solution of a suitable polymeric cationic hydroxy metal complex of a suitable metal, such as Al, Ti, Zr, Cr and mixtures of these metals (preferably Al or Al+Zr), followed by heating under such conditions so as to form pillars of an oxide or oxides of the metal interspersed between clay layers, as has been described in the patent literature, e.g., U.S. Pat. No. 4,719,191 and references cited therein. The specific preparation method of component (ii) is not considered critical. A preferred pillaring method employs an aged (more preferably aged for at least about 3 days at about 25° C.) aluminum hydroxy chloride solution, as is described in U.S. Pat. No. 4,637,991, the disclosure of which is herein incorporated by reference. In another preferred embodiment, an aged aluminum zicronium chloro hydroxy glycine complex (as described in Example I) is employed as a pillaring agent. Another suitable method for preparing a pillard clay material is described in U.S. Pat. No. 4,742,033, the disclosure of which is herein incorporated by reference. Generally, the surface area (measured by the BET adsorption method using $N_2$) of component (ii) is about 200–300 $m^2/g$.

In the oligomerization process of this invention, the simultaneous contacting of at least one $C_2$–$C_4$ monoolefin and the catalyst composition can be carried out under any suitable reaction conditions that result in the at least partial conversion of the said monoolefin to $C_5$–$C_{12}$ hydrocarbons. The reaction can be carried out as a batch process or as a continuous process. In a batch process, the olefin containing gas and catalyst composition can be added in any order to a reaction vessel, which is preferably equipped with mixing/agitating means so as to ensure contact between process ingredients (a) and (b). In a continuous process, which is presently preferred, a gas stream comprising at least one $C_2$–$C_4$ monoolefin is passed through a fixed bed containing the catalyst composition (optionally admixed with essentially inert refractory solids such as alumina, silica and the like), under such reaction conditions as to produce $C_5$–$C_{12}$ hydrocarbons.

Heating is generally required to accomplish a conversion of monoolefins to $C_5$–$C_{12}$ hydrocarbons. Any suitable temperature that will initiate and maintain a controllable reaction can be employed. Any feasible heating means can be utilized. It is within the scope of this invention to preheat the process ingredients before they are introduced into a reactor, which is heated to maintain a suitable temperature. Generally the reaction temperature ranges from about 100° F. to about 1,000° F., more preferably from about 300° F. to about 800° F.

The reaction pressure can vary from subatmospheric pressure to elevated pressure such as up to 500 psig. The selection of the reaction pressure will greatly depend on the reaction temperature, the volatility of process ingredients and products, and the specific reactor design. Generally, the pressure is approximately atmospheric (about 1 atm, 0 psig).

In a batch process, the reaction time, i.e., the time of contact between process ingredients (a) and (b), can vary from about 1 minute to about 20 hours and will preferably be in the range of about 1 to about 5 hours. The actual reaction time will greatly depend on the feed rate of reactants, the selection of an effective (yet safe) reaction temperature, the reaction pressure, and the extent of mixing and agitation during the reaction. In a continuous process, the gas hourly space velocity of the olefin-containing feed is generally in the range of from about 100 to 10,000 cc monoolefin/cc catalyst composition/hour, preferably from about 400 to about 2,000 cc/cc/hr.

The formed $C_5$–$C_{12}$ hydrocarbon (i.e., one hydrocarbon or a mixture of two or more than two hydrocarbons) can be separated from other components of the product (e.g., unreacted feed hydrocarbons and by-products such as ethylene and butenes) by any suitable separation means such as fractional distillation, or crystallization, or extraction with a suitable solvent (e.g., a liquid paraffin such as n-hexane) plus subsequent evaporation of the solvent. Unreacted feed hydrocarbons can be separated in a similar manner and can be recycled to the reaction zone with added fresh ingredients. The produced $C_5$–$C_{12}$ hydrocarbons can be recovered, and used as motor fuels. The $C_5$–$C_{12}$ hydrocarbons can be aliphatic, cycloaliphatic, olefinic, or mixtures thereof.

The following examples are presented to further illustrate this invention without unduly limiting the scope of the invention.

EXAMPLE I

This example illustrates the composition of various olefin oligomerization catalyst compositions.

Catalyst Composition A (Control) was a physical mixture (blend) of 0.77 grams of a 20–40 mesh silica gel and 0.75 grams of $WO_3$ on silica (containing 6 weight-% $WO_3$; having been prepared by impregnation of high surface silica gel with an aqueous ammonium metatungstate solution, followed by drying and calcining in air at 500° C.).

Catalyst Composition B (Control) was a physical mixture of 1.5 g Bentonite clay (unpillared) and 0.75 grams of $WO_3$ on silica.

Catalyst Composition C (Invention) was a physical mixture of 1.5 grams of a pillared clay and 0.75 grams of $WO_3$ on silica. The pillard clay was prepared as follows:

990 cc of a 50 weight-% aqueous solution of aluminum hydroxychloride having the approximate chemical formula of $Al_2(OH)_5Cl \cdot 2H_2O$ and a formula weight of 210 (provided by Reheis Chemical Company, Berkely Heights, N.J. under the trademark Chlorhydrol ®) was mixed with 9 liters of distilled water. This mixture was aged at room temperature for about 1 week. To this aged diluted Chlorhydrol ® solution was added 9 liters of distilled water and 1000 grams of a bentonite clay (supplied by American Colloid Company, Skokie, Ill.), and the formed slurry was stirred for 2 hours at 60° C. Then the Chlorhydrol ®-treated clay was filtered, the filter cake was dispersed in 5 liters of distilled water, filtered, redispersed in 5 liters of distilled water and filtered again. The thus washed filter cake of pillard clay was dried at 110° C., ground and sieved. A 10–20 mesh friction was calcined in air for 1 hour at 200° C. and then for 3 hours at 500° C.

Catalyst Composition D (Invention) was a physical mixture of 1.5 grams of another pillard clay and 0.75 grams of $WO_3$ on silica. The pillared clay present in D was prepared as follows:

856 cc of a 35 weight-% aqueous solution of an aluminum zirconium tetrachloro hydroxy glycine complex, containing about 9.7 millequivalents of ($Al^{+3}+Zr^{+4}$) per cc solution, having a weight ratio of Al:Zr of 3.6:1, containing 5.0–5.7 weight-% Al, 4.4–5.7 weight-% Zr, 3.6–4.7 weight-% glycine and 5.9–6.7 weight-% Cl (provided by Reheis Chemical Company under the trademark Rezal ® 36G) and was mixed with 9 liters of distilled water, stirred for 1 hour at room temperature, and allowed to age at room temperature for 6 days. 1000 grams of bentonite clay was added to this aged solution and the formed slurry was stirred for 2 hours at 60° C. The thus treated clay was separated, washed, ground, sieved, dried and calcined in accordance with the procedure described for Catalyst Composition C.

EXAMPLE II

This example illustrates the oligomerization of propylene, with and without added hydrogen gas, over Catalyst A and B.

All runs were made by passing a propylene feed through a vertical tubular quartz reactor (1 cm in diameter and 25 cm in length) positioned in a temperature-controlled electric furnace. In each run, the reactor contained a bed of the designated catalyst. Thermocouples were positioned in the catalyst bed to monitor the reaction temperature. Prior to each run, the catalyst was activated by heating in air at 500° C. for about 30 minutes and then in nitrogen at 500° C. for about 15 minutes. The propylene feed was of polymerization grade as sold by Phillips Petroleum Company of Bartlesville, Okla. The propylene feed was pretreated with activated Alcoa H151 alumina and activated magnesia prior to the oligomerization. The feed (14–15 psia) was passed downwardly through the vertically oriented tubular reactor.

Reaction product analyses were made by gas-liquid chromatography (GLC) employing a Hewlett-Packard model 5880A chromatograph having ⅛ inch by 20 ft. column packed with 19% BMEE+1% squalene on 60/80 Chrom P. Analyses were carried out isothermally at a temperature of about 30° to 40° C. with a helium carrier gas flow rate of about 20 mL/min. Hydrogen gas was introduced in small amounts during the oliogmerization reaction at various time intervals. Pertinent process parameters and product compositions are summarized in Table I.

TABLE I

| Run | Catalyst | Reaction Temp. (°C.) | % Conversion of Propylene | Mol % C5+ Hydrocarbons in Product |
|---|---|---|---|---|
| 1 (Control) | A | 500 | 49 | 5 |
| 2 (Control) | B | 500 | 37 | 3 |
| 3 (Invention) | C | 500 | 63 | 24 |
| 4 (Invention) | C | 400 | 32 | 19 |
| 5 (Invention) | D | 500 | 60 | 22 |

Test data in Table I show that mixtures of pillared clays and $WO_3/SiO_2$ (Runs 3-5) were more active catalysts for the conversion of propylene to $C_5+$ hydrocarbons than mixtures of unpillared clay and $WO_3/SiO_2$ (Run 2) or of silica and $WO_3/SiO_2$ (Run 1).

Reasonable variations and modifications can be made within the scope of the disclosure and the appended claims without departing from the spirit and scope of this invention.

That which is claimed is:

1. A composition of matter consisting essentially of a physical mixture of:
   (i) tungsten oxide being supported by a solid material consisting essentially of silica; and
   (ii) a pillared interlayered smectite clay.

2. A composition of matter in accordance with claim 1 wherein the weight percentage of tungsten oxide in compounds (i) is about 1-20 weight-% and the weight percentage of silica in component (i) is about 99-80 weight-%.

3. A composition of matter in accordance with claim 1 wherein said pillared interlayered smectite clay has been prepared by a process comprising the steps of reacting a smectite clay with an aqueous solution of a polymeric cationic hydroxy metal complex of at least one metal selected from the group consisting of Al, Ti, Zr and Cr, and heating the thus reacted smectite clay under such conditions as to form pillars of at least one oxide of said metal interspersed between layers of said clay.

4. A composition of matter in accordance with claim 3 wherein said smectite clay is bentonite and said at least one metal is selected from Al and mixtures of Al and Zr.

5. A composition of matter in accordance with claim 3 wherein said polymeric cationic hydroxy metal complex is an aluminum hydroxy chloride.

6. A composition of matter in accordance with claim 3 wherein said polymeric metal complex is an aluminum zirconium chloro hydroxy glycine chloride.

7. A composition of matter in accordance with claim 3 wherein said aqueous solution of said polymeric cationic hydroxy metal complex has been aged for at least about 3 days at about 25° C.

8. A composition of matter in accordance with claim 1 wherein the weight percentage of tungsten oxide in component (i) is about 2-8 weight-% and the weight percentage of silica in component (i) is about 98-92 weight-%.

9. A composition in accordance with claim 1 wherein the weight ratio of component (i) to component (ii) is in the range of from about 1:10 to about 5:1.

10. A composition of matter in accordance with claim 9, wherein said weight ratio is in the range of from about 1:4 to about 1:1.

11. A process for preparing a composition of matter consisting essentially of a physical mixture of (i) tungsten oxide being supported by a solid material consisting essentially of silica and (ii) a pillared interlayered smectite clay, said process comprising the steps of reacting a smectite clay with an aqueous solution of a polymeric cationic hydroxy metal complex of at least one metal selected from the group consisting of Al, Ti, Zr and Cr, and heating the thus reacted smectite clay under such conditions as to form pillars of at least one oxide of said metal interspersed between layers of said clay and to obtain component (ii).

12. A process in accordance with claim 11 wherein said smectite clay is bentonite and said at least one metal is selected from Al and mixtures of Al and Zr.

13. A process in accordance with claim 11 wherein said polymeric cationic hydroxy metal complex is an aluminum hydroxy chloride.

14. A process in accordance with claim 11 wherein said polymeric metal complex is an aluminum zirconium chloro hydroxy glycine complex.

15. A process in accordance with claim 11 wherein said aqueous solution of said polymeric cationic hydroxy metal complex has been aged for at least about 3 days at about 25° C.

16. A process in accordance with claim 11, said process comprising the steps of impregnating silica with a dissolved tungsten compound, drying the thus impregnated silica, and calcining the dried, impregnated silica at a temperature high enough to convert said tungsten compound to tungsten oxide and to obtain component (i).

17. A process in accordance with claim 16 wherein component (i) contains about 1-20 weight-% tungsten oxide.

18. A process in accordance with claim 16 additionally comprising the step of mixing components (i) and (ii), at a weight ratio of component (i) to component (ii) in the range of from about 1:10 to about 5:1.

* * * * *

UNITED STATES PATENT AND TRADEMARK OFFICE
CERTIFICATE OF CORRECTION

PATENT NO. : 4,948,768

DATED : August 14, 1990

INVENTOR(S) : Simon G. Kukes; Robert L. Banks; Jesse R. Harris

It is certified that error appears in the above-identified patent and that said Letters Patent is hereby corrected as shown below:

Claim 2, column 5, line 38, delete "compounds" and substitute --- component --- therefor.

Claim 6, column 6, line 3, delete "chloride" (at the end of the line) and substitute --- complex --- therefor.

Signed and Sealed this

Twenty-ninth Day of October, 1991

Attest:

HARRY F. MANBECK, JR.

*Attesting Officer*  *Commissioner of Patents and Trademarks*